(12) United States Patent
Teng et al.

(10) Patent No.: US 10,155,072 B2
(45) Date of Patent: Dec. 18, 2018

(54) VALVE MECHANISM FOR SUCTION AND IRRIGATION INSTRUMENTS

(71) Applicant: Taiwan Surgical Corporation, Hsinchu County (TW)

(72) Inventors: Ming-Chang Teng, Hsinchu (TW); Yu-Na Hsieh, Changhua County (TW)

(73) Assignee: Taiwan Surgical Corporation, Hsinchu County (TW)

( * ) Notice: Subject to any disclaimer, the term of this patent is extended or adjusted under 35 U.S.C. 154(b) by 200 days.

(21) Appl. No.: 15/013,117

(22) Filed: Feb. 2, 2016

(65) Prior Publication Data

US 2017/0100526 A1    Apr. 13, 2017

(30) Foreign Application Priority Data

Oct. 12, 2015    (TW) .............................. 104133334 A (51) Int. Cl.
*A61M 1/00*    (2006.01)
*A61M 39/22*    (2006.01)

(52) U.S. Cl.
CPC ........ *A61M 1/0062* (2013.01); *A61M 1/0043* (2013.01); *A61M 1/0064* (2013.01); *A61M 39/22* (2013.01); *A61M 39/223* (2013.01); *A61M 2039/224* (2013.01)

(58) Field of Classification Search
CPC .............. A61M 1/0062; A61M 39/223; A61M 1/0058; A61M 1/0064; A61M 1/0043; A61C 17/0202; A61C 17/0217
See application file for complete search history.

(56) References Cited

U.S. PATENT DOCUMENTS

| | | | |
|---|---|---|---|
| 4,526,573 A | | 7/1985 | Lester et al. |
| 5,254,083 A | * | 10/1993 | Gentelia ............. A61M 1/0064 251/7 |
| 2010/0094200 A1 | | 4/2010 | Dean et al. |
| 2011/0230823 A1 | | 9/2011 | Simonsen |
| 2013/0303979 A1 | | 11/2013 | Stieglitz et al. |
| 2015/0094709 A1 | * | 4/2015 | Elliott ................... A61B 18/14 606/34 |

FOREIGN PATENT DOCUMENTS

| | | |
|---|---|---|
| CN | 1153065 A | 7/1997 |
| CN | 201631912 U | 11/2010 |
| CN | 201668784 U | 12/2010 |
| CN | 102284090 B | 2/2014 |
| CN | 204364119 U | 6/2015 |
| CN | 103203069 B | 8/2015 |
| KR | 20130090393 A | 8/2013 |
| TW | M306863 B | 3/2007 |

* cited by examiner

*Primary Examiner* — Laura A Bouchelle
*Assistant Examiner* — Tasnim Mehjabin Ahmed
(74) *Attorney, Agent, or Firm* — Alan D. Kamrath; Kamrath IP Lawfirm, P.A.

(57) ABSTRACT

A valve mechanism for a suction instrument or an irrigation instrument includes a valve object; a first piston moveably disposed in the valve object; a second piston moveably disposed in the valve object; and a piston buckling unit pivoting on an outside of the valve object. When the first piston is pressed, the first piston moves downward, and a first buckle on the first piston is fixed on a third buckle of the piston buckling unit to open an irrigating pathway. When the second piston is pressed, the second piston moves downward, and a second buckle on the second piston is fixed on another third buckle of the piston buckling unit to open a suction pathway.

14 Claims, 5 Drawing Sheets

VALVE MECHANISM FOR SUCTION AND IRRIGATION INSTRUMENTS

CROSS REFERENCE TO RELATED APPLICATION

This application claims the benefits of Taiwan Patent Application Serial Number 104133334, filed on Oct. 12, 2015, the subject matter of which is incorporated herein by reference.

BACKGROUND OF THE INVENTION

1. Field of the Invention

The present invention relates to a valve mechanism for suction and irrigation instruments. More specifically, the valve mechanism of the present invention is equipped with buckles to maintain the valve mechanism in an opened suction or irrigation state.

2. Description of Related Art

In laparoscopic operations, a valve mechanism for suction and irrigation instruments is usually used to wash the abdominal cavity or remove waste materials in the abdominal cavity.

Like traditional operations, the irrigation step using saline solution or the suction step for removing waste blood or secretion is also performed in the laparoscopic operations. However, the difference between the traditional operations and the laparoscopic operations is that the suction and irrigation step has to be performed by a single conduit during the laparoscopic operations. Hence, the switch of the suction and irrigation pathways is necessary, and a liquid pump also has to be used. Hence, for the laparoscopic operations, a device with dual functions of suction and irrigation is usually used to wash the abdominal cavity or remove waste material. Especially, if the operations are complex, such as acute cholecystitis operations, the suction and irrigation steps have to be continuously performed. In this case, the device with dual functions of suction and irrigation can increase the operation efficiency.

During the operations, the suction and irrigation pathways have to be switched many times. If the conventional suction and irrigation device is used, continuous suction and irrigation cannot be achieved, and the suction and irrigation pathway cannot be switched rapidly. In addition, the user has to continuously press the suction or irrigation piston, resulting in decreased convenience.

Hence, it is desirable to provide a novel valve mechanism for a suction instrument and an irrigation instrument, which can accomplish the purpose of continuous, suction and irrigation and which can easily switch, in order to improve the user's convenience and using flexibility.

SUMMARY OF THE INVENTION

An object of the present invention is to provide a valve mechanism for at least one of a suction instrument and an irrigation instrument, which is equipped with buckles for fixing pistons and has a function of easily switching to improve the user's convenience.

The valve mechanism for at least one of a suction instrument and an irrigation instrument comprises: a valve object comprising a proximal conduit, a suction conduit for connecting with a suction instrument, and an irrigation conduit for connecting with an irrigation instrument; a first piston moveably disposed in the valve object and comprising a first irrigation through-going opening and a first suction through-going opening, with at least one first buckle disposed on a first sidewall of the first piston; a second piston moveably disposed in the valve object and comprising a second irrigation through-going opening and a second suction through-going opening, with at least one second buckle disposed on a second sidewall of the second piston; and a piston buckling unit pivoting on an outside of the valve object and comprising plural third buckles. When the first piston is pressed, the first piston moves downward, and the first buckle on the first piston is fixed on the third buckle of the piston buckling unit corresponding thereto to open an irrigating pathway between the first irrigation through-going opening, the second irrigation through-going opening, the proximal conduit and the irrigation conduit. When the second piston is pressed, the second piston moves downward, and the second buckle on the second piston is fixed on another third buckle of the piston buckling unit corresponding thereto to open a suction pathway between the first suction through-going opening, the second suction through-going opening, the proximal conduit and the suction conduit.

In the valve mechanism of the present invention, the first buckle and the second buckle are respectively formed on the first piston and the second piston, and the piston buckling unit is equipped with the third buckles. When the first piston or the second piston is pressed to move downward, the first buckle or the second buckle can respectively be buckled up the third buckle. Therefore, the position of the first piston or the second piston can be fixed. Hence, the user does not have to continuously press the first piston and/or the second piston, and the user's convenience can further be improved.

In addition, in the valve mechanism of the present invention, the piston buckling unit may further comprise a release unit. When the first piston is in a pressed condition, by pressing the release unit, the third buckle is released from the first buckle, and the first piston moves upward. When the second piston is in a pressed condition, by pressing the release unit, the third buckle is released from the second buckle, and the second piston moves upward.

In the valve mechanism of the present invention, the first irrigation through-going opening is preferably disposed below the first suction through-going opening. In addition, the second irrigation through-going opening is preferably disposed below the second suction through-going opening.

In the valve mechanism of the present invention, both the first suction through-going opening and the second suction through-going opening preferably are linear conduits. When the second piston moves downward, the suction pathway between the first suction through-going opening, the second suction through-going opening, the proximal conduit and the suction conduit is a linear suction pathway.

In the valve mechanism of the present invention, the valve object may further comprise a transferring conduit, and the second irrigation through-going opening is a bending conduit. When the first piston moves downward, the irrigating pathway is formed between the first irrigation through-going opening, the second irrigation through-going opening, the transferring conduit, the proximal conduit and the irrigation conduit.

In the valve mechanism of the present invention, the first piston may have a first separation wall, which closes an end of the irrigation conduit when the first piston is not pressed.

In addition, in the valve mechanism of the present invention, the second irrigation through-going opening may have two ends, and an angle is included between opening directions of the two ends. In one preferred embodiment, one of the ends of the second irrigation through-going opening is opposite to a second separation wall, and the second separation wall closes an end of the suction conduit when the second piston is not pressed.

Furthermore, in the valve mechanism of the present invention, the first buckle on the first piston can be released from the third buckle of the piston buckling unit by directly pressing the second piston when the first buckle is fixed on the third buckle, and the second buckle on the second piston is released from the third buckle of the piston buckling unit by directly pressing the first piston when the second buckle is fixed on the third buckle.

Other objects, advantages, and novel features of the invention will become more apparent from the following detailed description when taken in conjunction with the accompanying drawings.

DETAILED DESCRIPTION OF THE PREFERRED EMBODIMENTS

The present invention has been described in an illustrative manner, and it is to be understood that the terminology used is intended to be in the nature of description rather than of limitation. Many modifications and variations of the present invention are possible in light of the above teachings. Therefore, it is to be understood that within the scope of the appended claims, the invention may be practiced otherwise than as specifically described.

Furthermore, the ordinal numbers such as "first" and "second" used in the present specification and the appended claims are used to modify the units in the appended claims. The ordinal numbers themselves do not mean or represent the claimed units having ordinal numbers, and do not represent the order of one claimed unit to another claimed unit or the sequence of the manufacturing process. The ordinal numbers are used only for naming one claimed unit to clearly distinguish the claimed unit from the other claimed unit having the same term.

Figure 1:
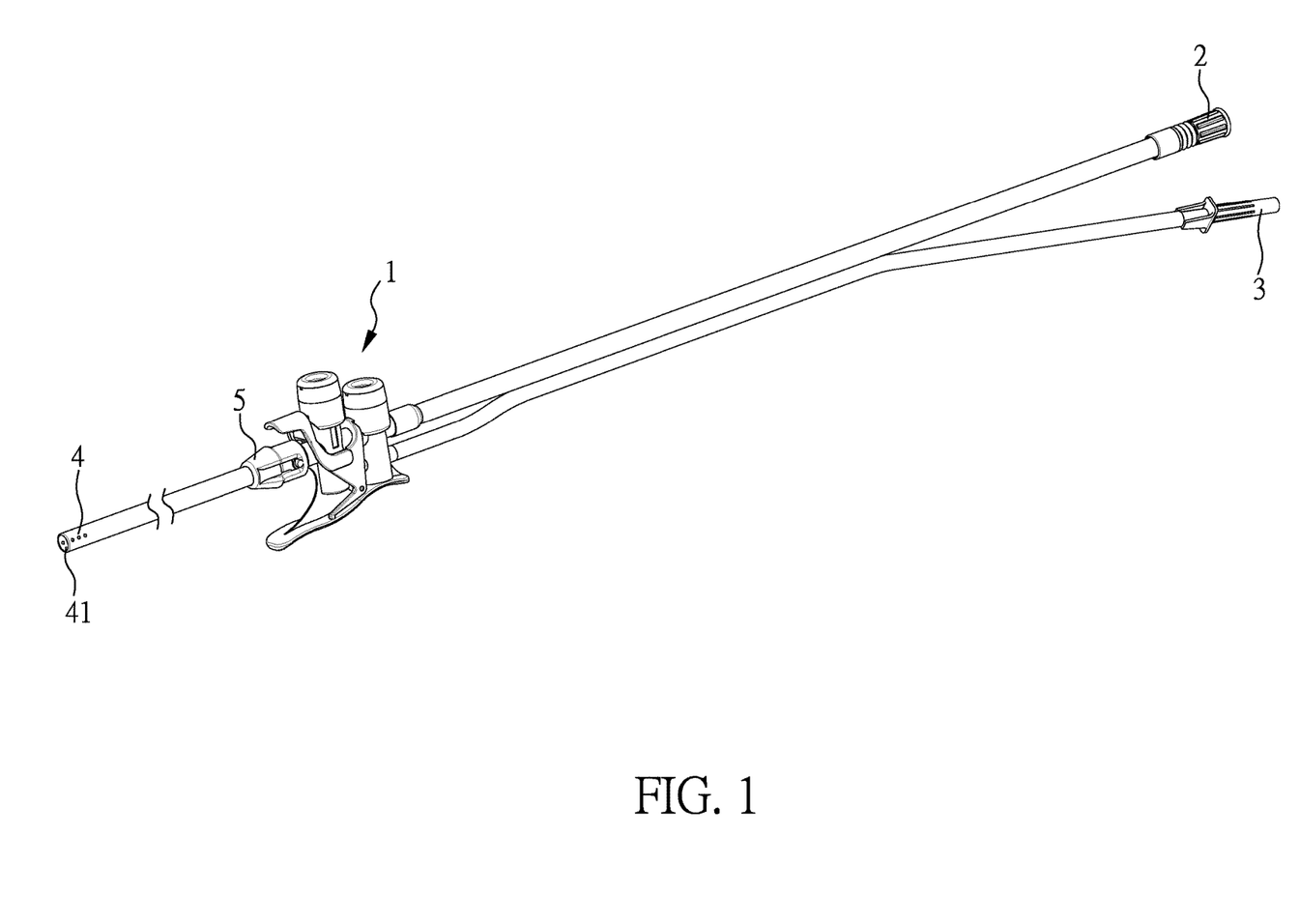
FIG. 1 is a perspective view showing a valve mechanism according to one preferred embodiment of the present invention.

FIG. 1 is a perspective view showing a valve mechanism for a suction instrument or an irrigation instrument according to one preferred embodiment of the present invention. As shown in FIG. 1, the valve mechanism 1 is connected to an elongated tube 4 with a fixing unit 5, and the fixing unit 5 can keep the relative position between the valve mechanism 1 and the elongated tube 4. The elongated tube 4 has an opening 41. A user can perform a suction or irrigation step by placing the opening 41 on waste material to be removed or a target to be washed.

Figure 2:
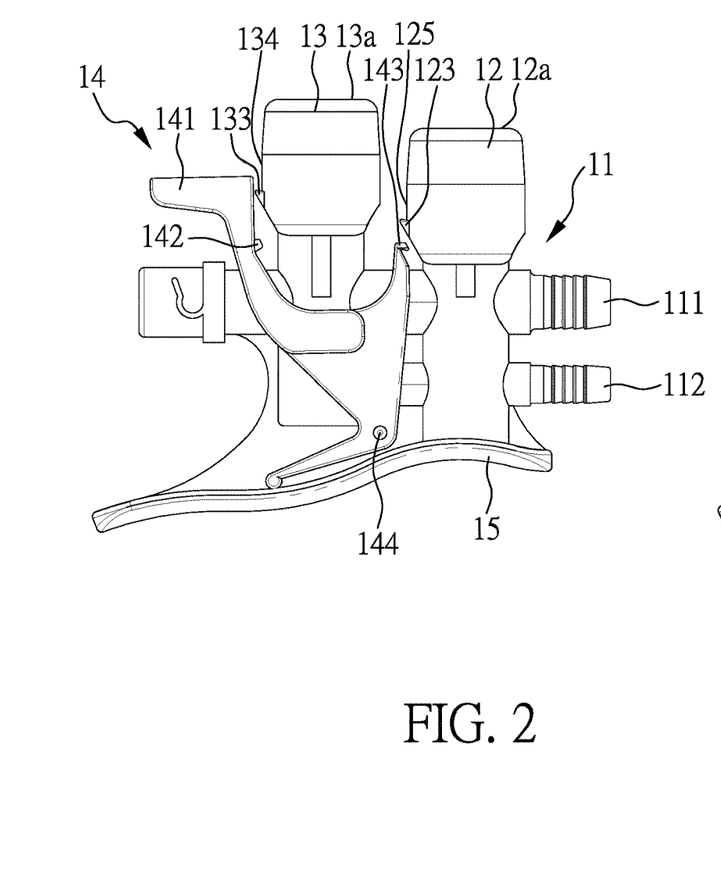
FIG. 2 is a perspective view showing the valve mechanism according to one preferred embodiment of the present invention.

FIG. 2 is a perspective view showing the valve mechanism according to one preferred embodiment of the present invention. As shown in FIGS. 1 and 2, the valve mechanism 1 of the present embodiment comprises a valve object 11, which comprises a suction conduit 111 and an irrigation conduit 112. The suction conduit 111 is connected to a suction tube 2, and is further connected to a suction instrument (not shown in the figure) (for example, a waste suction instrument) via the suction tube 2. The irrigation conduit 112 is connected to an irrigation tube 3, and is further connected to an irrigation instrument (not shown in the figure) (for example, a liquid pump) via the irrigation tube 3. In the present embodiment, the example that the valve mechanism 1 is connected to both the suction tube 2 and the irrigation tube 3 is shown. Even though the valve mechanism 1 of the present embodiment can achieve the suction and irrigation functions, in some case, only one of these functions is used. In this case, the suction tube 2 and the irrigation tube 3 are not necessarily assembled on the valve mechanism 1 simultaneously.

In addition, as shown in FIG. 2, the valve mechanism 1 of the present embodiment comprises not only the valve object 11 but also other components. Herein, the valve mechanism 1 of the present embodiment further comprises: a first piston 12 moveably disposed in the valve object 11 and comprising at least one first buckle 123 disposed on a first sidewall 125 of the first piston 12; a second piston 13 moveably disposed in the valve object 11 and comprising at least one second buckle 133 disposed on a second sidewall 134 of the second piston 13; and a piston buckling unit 14 pivoting on an outside of the valve object 11 via a pivot 144 and comprising plural third buckles 142, 143. In addition, the piston buckling unit 14 further comprises a release unit 141. The arrangement of the release unit 141 is not particularly limited and may be disposed adjacent to the first piston 12 or the second piston 13, as shown in FIGS. 2 and 3.

Figure 3:
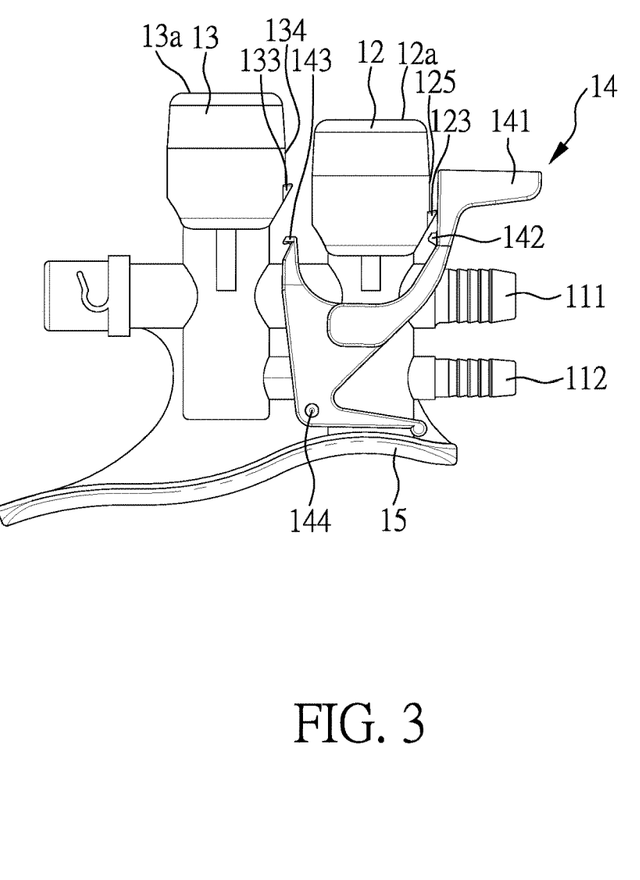
FIG. 3 is a perspective view showing another valve mechanism according to another preferred embodiment of the present invention.

Furthermore, as shown in FIGS. 2 and 3, the valve mechanism of the present embodiment may further comprise a supporting unit 15. When the user operates the valve mechanism of the present embodiment, the user's hand can hold this supporting unit 15. Therefore, the user's fingers can easily press the first piston 12, the second piston 13 and the release unit 141.

The operations of the valve mechanisms shown in FIGS. 2 and 3 are the same. Hence, hereinafter, only the operation of the valve mechanism shown in FIG. 2 is explained below, and the operation of the valve mechanism shown in FIG. 3 is not repeated again.

Figure 4:
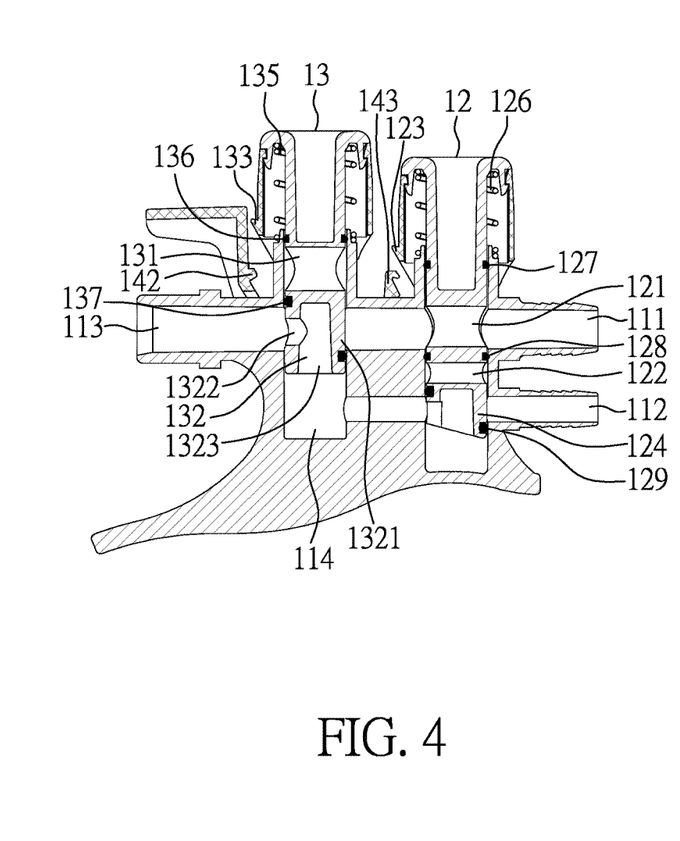
FIG. 4 is a cross-sectional view showing the un-operated valve mechanism according to one preferred embodiment of the present invention.

FIG. 4 is a cross-sectional view showing the valve mechanism in an un-operated state according to one preferred embodiment of the present invention. As shown in FIGS. 2 and 4, the valve mechanism of the present embodiment comprises: a valve object 11 comprising a proximal conduit 113, a suction conduit 111 for connecting with a suction instrument (not shown in the figure), and an irrigation conduit 112 for connecting with an irrigation instrument (not shown in the figure); a first piston 12 moveably disposed in the valve object 11 and comprising a first irrigation through-going opening 122 and a first suction through-going opening 121, with at least one first buckle 123 disposed on a first sidewall 125 of the first piston 12; a second piston 13 moveably disposed in the valve object 11 and comprising a second irrigation through-going opening 132 and a second suction through-going opening 131, with at least one second buckle 133 disposed on a second sidewall 134 of the second piston 13; and a piston buckling unit 14 pivoting on an outside of the valve object 11 and comprising plural third buckles 142, 143. In the present embodiment, in order to match the positions of the suction conduit 111 and the irrigation conduit 112, the first irrigation through-going opening 122 is disposed below the first suction through-going opening 121, and the second irrigation through-going opening 132 is disposed below the second suction through-going opening 131.

In addition, as shown in FIG. 4, the first piston 12 has a first separation wall 124, which closes an end of the irrigation conduit 112 before operating the valve mechanism (more specifically, the first piston 12 is not pressed) to close the irrigating pathway. The second piston 13 also has a second separation wall 1321, which closes an end of the suction conduit 111 before operating the valve mechanism (more specifically, the second piston 13 is not pressed) to close the suction pathway.

Furthermore, as shown in FIG. 4, the first piston 12 comprises an elastic unit 126 to provide a restoring force for the first piston 12 moving upward. In the present embodiment, the elastic unit 126 is a spring. The second piston 13 also comprises another elastic unit 135 to provide a restoring force for the second piston 13 moving upward. In the present embodiment, the elastic unit 135 is also a spring. In addition, the first piston 12 further comprises sealing rings 127, 128, 129, and the second piston 13 also comprises sealing rings 136, 137, to prevent rftheli liquid leakage from the irrigation and suction pathways.

Figure 5:
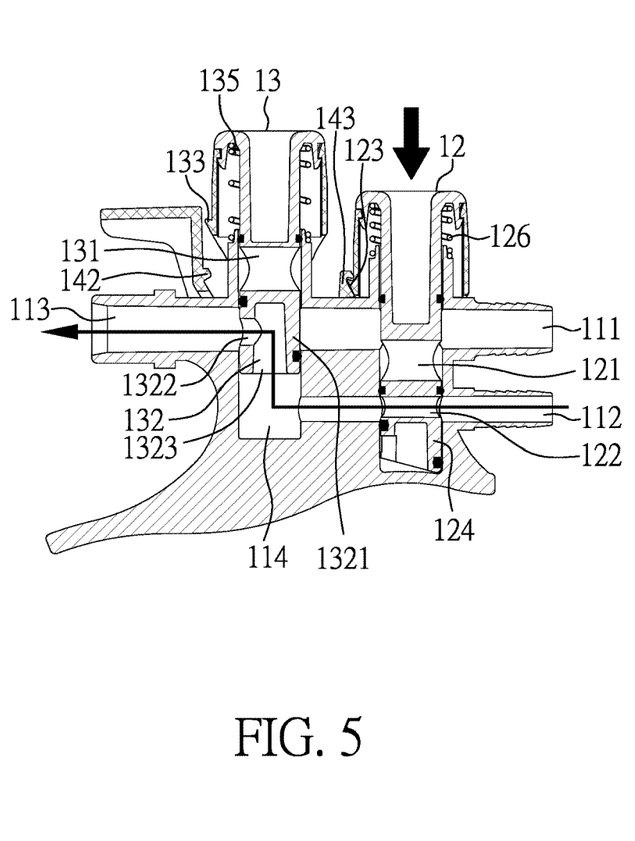
FIG. 5 is a cross-sectional view showing the valve mechanism in an irrigation state according to one preferred embodiment of the present invention.

FIG. 5 is a cross-sectional view showing the valve mechanism in an irrigation state according to one preferred embodiment of the present invention. As shown in FIGS. 2 and 5, when the user presses on a surface 12a of the first piston 12, the first piston 12 moves downward, compresses the elastic unit 126, and drives the piston buckling unit 14. Then, the first buckle 123 is buckled on the third buckle 143 corresponding thereto to maintain the position of the first piston 12, and an irrigating pathway between the first irrigation through-going opening 122, the second irrigation through-going opening 132, the proximal conduit 113 and the irrigation conduit 112 is opened. In addition, since the first buckle 123 is buckled on the third buckle 143 corresponding thereto, the irrigating pathway can maintain in an open state. Therefore, the user does not have to press the first piston 12 continuously. In the present embodiment, the valve object 11 further comprises a transferring conduit 114, and the second irrigation through-going opening 132 is a bending conduit. When the first piston 12 moves downward, the opened irrigating pathway is formed between the first irrigation through-going opening 122, the second irrigation through-going opening 132, the transferring conduit 114, the proximal conduit 113 and the irrigation conduit 112.

In the present embodiment, the second irrigation through-going opening 132 has two ends 1322, 1323, and an angle is included between opening directions of the two ends 1322, 1323. In addition, the end 1322 of the second irrigation through-going opening 132 is opposite to a second separation wall 1321, and the second separation wall 1321 closes an end of the suction conduit 111 when the second piston 13 is not pressed, as shown in FIG. 4. In the present embodiment, the angle included between opening directions of the two ends 1322, 1323 of the second irrigation through-going opening 132 is about 90 degrees, so the second irrigation through-going opening 132 is a bending through-going opening with an L-shape direction of flow. However, in other embodiments of the preset present invention, the angle included between opening directions of the two ends 1322, 1323 of the second irrigation through-going opening 132 is not limited to 90 degrees, and can be other angles (preferably, an obtuse angle), as long as the second separation wall 1321 can close an end of the suction conduit 111 when the second piston 13 is not pressed.

Figure 6:
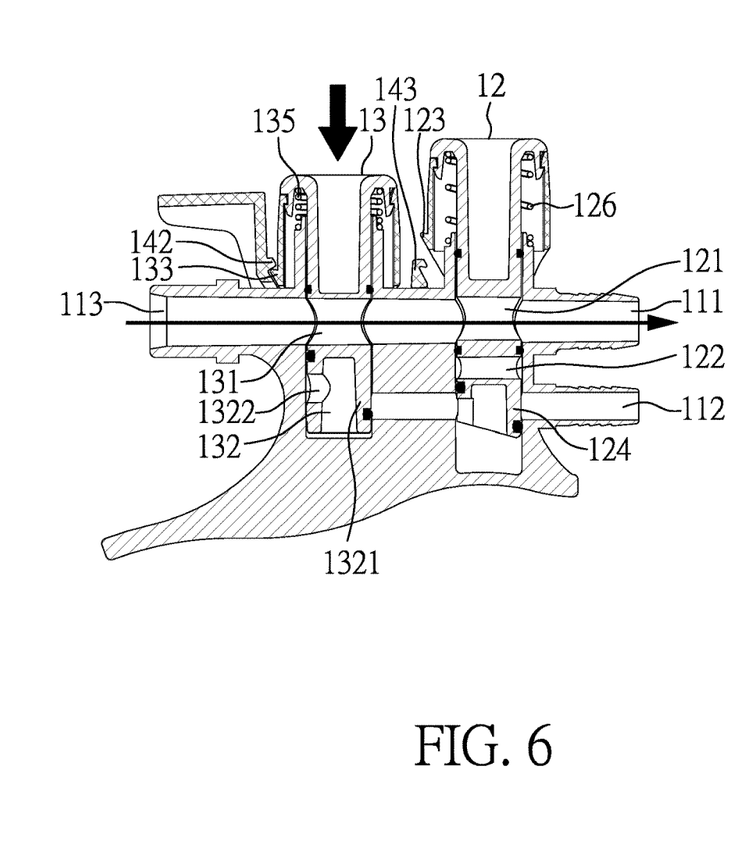
FIG. 6 is a cross-sectional view showing the valve mechanism in a suction state according to one preferred embodiment of the present invention.

FIG. 6 is a cross-sectional view showing the valve mechanism in a suction state according to one preferred embodiment of the present invention. As shown in FIGS. 2 and 6, when the user presses on a surface 13a of the second piston 13, the second piston 13 moves downward, compresses the elastic unit 135, and drives the piston buckling unit 14. Then, the second buckle 133 is buckled on the third buckle 142 corresponding thereto to maintain the position of the second piston 13, and a suction pathway between the first suction through-going opening 121, the second suction through-going opening 131, the proximal conduit 113 and the suction conduit 111 is opened. In addition, since the second buckle 133 is buckled on the third buckle 142 corresponding thereto, the suction pathway can maintain in an open state. Therefore, the user does not have to press the second piston 13 continuously. In the present embodiment, both the first suction through-going opening 121 and the second suction through-going opening 131 are linear conduits. When the second piston 13 moves downward, the suction pathway between the first suction through-going opening 121, the second suction through-going opening 131, the proximal conduit 113 and the suction conduit 111 is a linear suction pathway. When the valve mechanism of the present embodiment is used to perform a suction operation, in the case that the suction pathway is not a linear pathway, solids contained in the waste material may block the suction pathway. Hence, in the present embodiment, the suction pathway is designed into a linear pathway to prevent the blocking problem.

In the valve mechanism of the present invention, "the first piston 12 or the second piston 13 moving downward" refers to the moving direction of the first piston 12 or the second piston 13 when pressing the first piston 12 or the second piston 13, as shown in FIGS. 2, 5 and 6.

Figure 7:
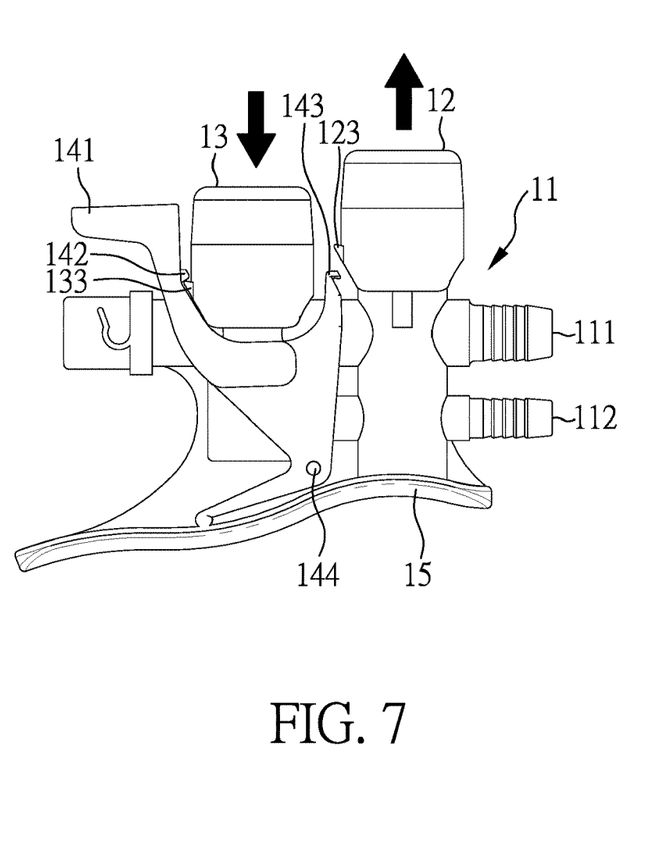
FIG. 7 is a perspective view showing the valve mechanism when switching a first piston and a second piston according to one preferred embodiment of the present invention.
Figure 8:
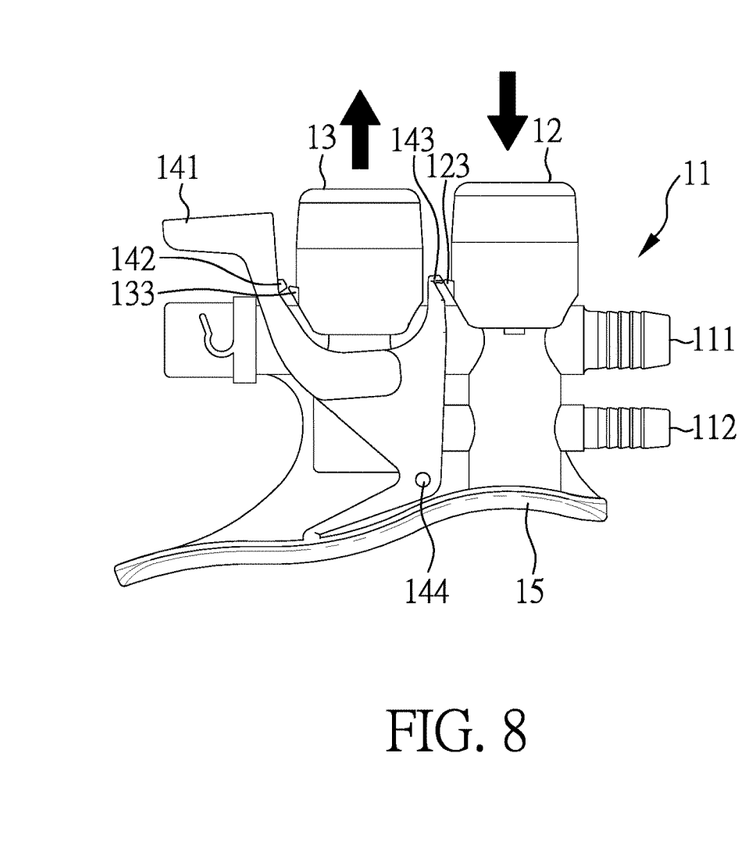
FIG. 8 is a perspective view showing the valve mechanism when switching the first piston and the second piston according to one preferred embodiment of the present invention.

FIGS. 7 and 8 are perspective views showing the valve mechanism when switching the first piston and the second piston according to one preferred embodiment of the present invention. In the present embodiment, the piston buckling unit 14 further comprises a release unit 141. As shown in FIGS. 5 and 7, when the user presses the first piston 12 to open the irrigation pathway, the first buckle 123 is buckled on the third buckle 143 corresponding thereto. When the user wants to switch the irrigation pathway into the suction pathway, the user can directly press the second piston 13, and the first buckle 123 is released from the third buckle 143. Then, the first piston 12 moves upward via the restoring force of the elastic unit 126, the second buckle 133 is buckled on the third buckle 142 corresponding thereto, and the valve mechanism is switched into the suction state. As shown in FIGS. 6 and 8, when the user presses the second buckle 133 to open the suction pathway, the second buckle 133 is buckled on the third buckle 142 corresponding thereto. When the user wants to switch the suction pathway into the irrigation pathway, the user can directly press the first piston 12, and the second buckle 133 is released from the third buckle 142. Then, the second piston 13 moves upward via the restoring force of the elastic unit 135, the first buckle 123 is buckled on the third buckle 143 corresponding thereto, and the valve mechanism is switched into the irrigation state.

Figure 9:
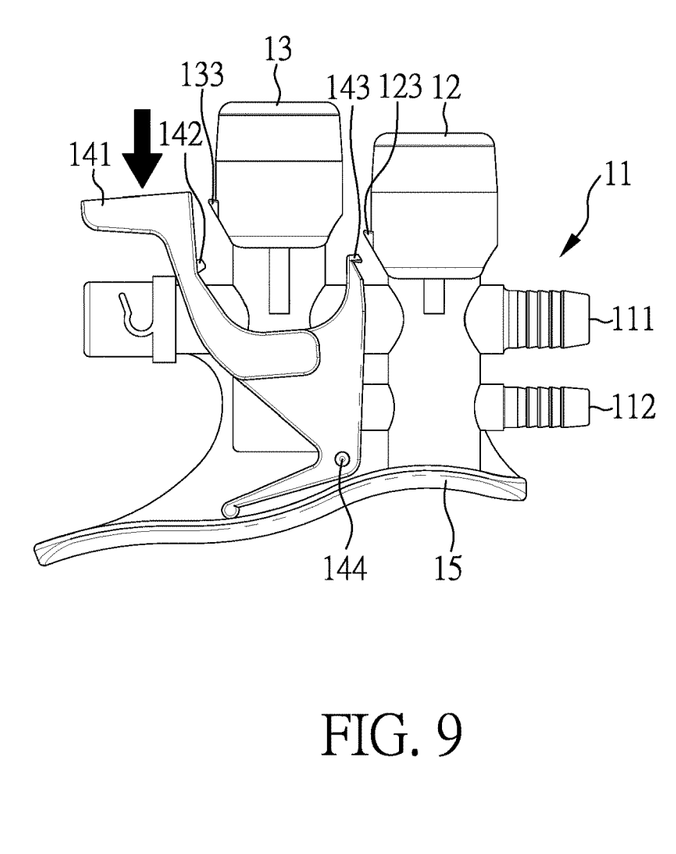
FIG. 9 is a perspective view showing the valve mechanism when releasing the first piston and/or the second piston by a piston buckling unit according to one preferred embodiment of the present invention.

FIG. 9 is a perspective view showing the valve mechanism when releasing the first piston and/or the second piston by the piston buckling unit according to one preferred embodiment of the present invention. As shown in FIGS. 5, 6 and 9, in either the irrigation state when the first piston 12 is pressed or the suction state when the second piston 13 is pressed, pressing the release unit 141 can make the third buckles 142, 143 separate from the first buckle 123 or the second buckle 133 if the user desires to finish the irrigation or suction step. Then, the first piston 12 or the second piston 13 moves upward via the restoring force of the elastic unit 126 or the elastic unit 135 to close the irrigation or suction pathway. Therefore, the irrigation or suction step is finished.

Hence, in the valve mechanism of the present invention, the first piston 12 and the second piston 13 respectively comprise the first buckle 123 and the second buckle 133, and the piston buckling unit 14 comprises third buckles 142, 143. When the first piston 12 or the second piston 13 is pressed and moves downward, the first buckle 123 or the second buckle 133 can be buckled on the third buckles 142, 143 to fix the position of the first piston 12 or the second piston 13. Hence, the user does not have to continuously press the first piston 12 or the second piston 13, and the user's convenience can be improved. In addition, the first piston 12 and/or the second piston 13 can be easily released by pressing the release unit 141 of the piston buckling unit 14, and the suction or irrigation pathway can be easily closed. When the user wants to switch the irrigation pathway or the suction pathway, the user can directly press the first piston 12 to make the piston buckling unit 14 release the second piston 13 and buckle the first piston 12, or directly press the second piston 13 and make the piston buckling unit 14 release the first piston 12 and buckle the second piston 13. Hence, the irrigation and suction states can be switched rapidly, and the use efficiency can be improved. Meanwhile, in the valve mechanism of the present invention, the suction pathway is designed into a linear pathway, so the problem that the solids containing in the waste material may block the suction pathway can be prevented.

Although the present invention has been explained in relation to its preferred embodiments, it is to be understood that many other possible modifications and variations can be made without departing from the spirit and scope of the invention as hereinafter claimed.

What is claimed is:

1. A valve mechanism for a suction instrument or an irrigation instrument, comprising:
    a valve object comprising a proximal conduit, a suction conduit for connecting with the suction instrument, and an irrigation conduit for connecting the irrigation instrument;
    a first piston moveably disposed in the valve object and comprising a first irrigation through-going opening and a first suction through-going opening moveable relative to the valve object with the first piston, wherein at least one first buckle is disposed on and protrudes from a first sidewall of the first piston;
    a second piston moveably disposed in the valve object and comprising a second irrigation through-going opening and a second suction through-going opening moveable relative to the valve object with the second piston, wherein at least one second buckle is disposed on a second sidewall of the second piston; and
    a piston buckling unit fixed to and pivotal on an outside of the valve object and comprising two third buckles,
    wherein when the first piston is pressed, the first piston, the first irrigation through-going opening and the first suction through-going opening move downward and the first buckle on the first piston is fixed on one of the two third buckles of the piston buckling unit to open an irrigating pathway between the first irrigation through-going opening, the second irrigation through-going opening, the proximal conduit and the irrigation conduit; and
    wherein when the second piston is pressed, the second piston, the second irrigation through-going opening and the first suction through-going opening move downward and the second buckle on the second piston is fixed on another of the two third buckles of the piston buckling unit to open a suction pathway between the first suction through-going opening, the second suction through-going opening, the proximal conduit and the suction conduit.

2. The valve mechanism as claimed in claim 1, wherein the piston buckling unit further comprises a release unit; and wherein when the release unit is pressed, the one of the two third buckles is released from the first buckle and the first piston moves upward.

3. The valve mechanism as claimed in claim 1, wherein the piston buckling unit further comprises a release unit; and wherein when the release unit is pressed, the other of the two third buckles is released from the second buckle and the second piston moves upward.

4. The valve mechanism as claimed in claim 1, wherein the first irrigation through-going opening is disposed below the first suction through-going opening when the first piston moves downward.

5. The valve mechanism as claimed in claim 1, wherein the second irrigation through-going opening is disposed below the second suction through-going opening when the second piston moves downward.

6. The valve mechanism as claimed in claim 1, wherein both the first suction through-going opening and the second suction through-going opening are linear conduits; and wherein when the second piston moves downward, the suction pathway between the first suction through-going opening, the second suction through-going opening, the proximal conduit and the suction conduit is a linear suction pathway.

7. The valve mechanism as claimed in claim 1, wherein the valve object further comprises a transferring conduit, wherein the second irrigation through-going opening is a bending conduit; and wherein when the first piston moves downward, the irrigating pathway is formed between the first irrigation through-going opening, the second irrigation through-going opening, the transferring conduit, the proximal conduit and the irrigation conduit.

8. The valve mechanism as claimed in claim 1, wherein the first piston has a first separation wall which closes an end of the irrigation conduit when the first piston is not pressed.

9. The valve mechanism as claimed in claim 1, wherein the second irrigation through-going opening has two ends, and wherein an angle is included between opening directions of the two ends.

10. The valve mechanism as claimed in claim 9, wherein one of the two ends of the second irrigation through-going opening is opposite to a second separation wall, and wherein the second separation wall closes an end of the suction conduit when the second piston is not pressed.

11. The valve mechanism as claimed in claim 1, wherein the at least one first buckle on the first piston is released from the one of the two third buckles of the piston buckling unit by directly pressing the second piston when the at least one first buckle is fixed on the one of the two third buckles.

12. The valve mechanism as claimed in claim 1, wherein the at least one second buckle on the second piston is released from the other of the two third buckles of the piston buckling unit by directly pressing the first piston when the at least one second buckle is fixed on the other of the two third buckles.

13. The valve mechanism as claimed in claim 1, wherein the two third buckles are separate from each other and independently pivotal on the outside of the valve object.

14. The valve mechanism as claimed in claim 1, wherein the first and second piston each includes a top which is pressed, with the two third buckles having the at least one first and second buckles respectively located intermediate and spaced from the tops of the first and second pistons and the valve object.

* * * * *